United States Patent [19]

Immel et al.

[11] Patent Number: 5,344,987

[45] Date of Patent: Sep. 6, 1994

[54] PROCESS FOR PREPARING DIPHENYLAMINES

[75] Inventors: Otto Immel; Gerhard Darsow; Hans-Josef Buysch, all of Krefeld, Fed. Rep. of Germany

[73] Assignee: Bayer Aktiengesellschaft, Leverkusen, Fed. Rep. of Germany

[21] Appl. No.: 92,735

[22] Filed: Jul. 16, 1993

[30] Foreign Application Priority Data

Jul. 23, 1992 [DE] Fed. Rep. of Germany ....... 4224366

[51] Int. Cl.$^5$ .................. C07C 209/24; C07C 209/72
[52] U.S. Cl. ..................... 564/735; 564/396; 564/397; 564/398; 564/431; 564/433
[58] Field of Search ............... 564/396, 397, 398, 431, 564/433, 435

[56] References Cited

U.S. PATENT DOCUMENTS

| 3,219,702 | 11/1965 | Van Verth et al. | 564/398 |
| 3,219,704 | 11/1965 | Wilder et al. | 564/398 |
| 4,057,581 | 11/1977 | Krall et al. | 564/433 |
| 4,429,157 | 1/1984 | Disteldorf et al. | 564/397 X |
| 4,729,977 | 3/1988 | Immel et al. | 502/170 |
| 4,902,661 | 2/1990 | Immel et al. | 502/184 |
| 5,196,592 | 3/1993 | Immel et al. | 564/433 X |

FOREIGN PATENT DOCUMENTS

| 103990 | 8/1983 | European Pat. Off. |
| 0208933 | 1/1987 | European Pat. Off. |
| 0530736 | 7/1931 | Fed. Rep. of Germany |
| 1493942 | 3/1969 | Fed. Rep. of Germany |
| 2249089 | 4/1973 | Fed. Rep. of Germany |
| 2331878 | 1/1974 | Fed. Rep. of Germany |
| 2520893 | 11/1976 | Fed. Rep. of Germany |
| 3801754 | 7/1989 | Fed. Rep. of Germany |
| 4107395 | 9/1992 | Fed. Rep. of Germany |
| 1382206 | 1/1975 | United Kingdom |
| 1402707 | 8/1975 | United Kingdom |

Primary Examiner—Richard L. Raymond
Attorney, Agent, or Firm—Sprung Horn Kramer & Woods

[57] ABSTRACT

Optionally substituted diphenylamines can be obtained by reacting optionally substituted anilines with optionally substituted cyclohexanones over a supported catalyst at 200°–450° C. and 0.1–20 bar, the supported catalyst containing one or more metals having a dehydrogenating action selected from the group Ru, Pd, Os, Ir, Pt, Fe, Co, Ni, Re, Mn, Cu, Ag, Cr and Ce.

20 Claims, No Drawings

PROCESS FOR PREPARING DIPHENYLAMINES

BACKGROUND OF THE INVENTION

1. Field of the Invention

The invention relates to a process for preparing optionally substituted diphenylamines by reacting the corresponding cyclohexanones and anilines in the presence of a supported catalyst containing one or more metals of the type described below having a dehydrogenating action.

2. Description of the Related Art

A process for preparing diphenylamine and its derivatives is known from DE-OS (German Published Specification) 2,331,878, in which imines such as N-cyclohexylidene-aniline and its derivatives are used as starting materials and are dehydrogenated in the gaseous phase in the presence of supported catalysts based on nickel, palladium, or copper-chromium.

Furthermore, it is known from DE-OS (German Published Specification) 2,520,893 to prepare diphenylamine by catalytic dehydrogenation of compounds and/or mixtures of compounds comprising wholly or partly hydrogenated diphenylamine, in the presence of a dehydrogenation catalyst containing nickel-chromium, aluminium, copper, manganese and alkali metal. Binuclear aromatic imines are mentioned as such compounds in the examples of implementation.

According to DE-OS (German Published Specification) 1,493,942 the preparation of diphenylamine from cyclohexanone and aniline is carried out in the liquid phase via the intermediate stage of the associated Schiff base in the presence of a dehydrogenation catalyst and a hydrogen acceptor. Such a process is too costly for technical implementation.

Also, the dehydrogenation of dicyclohexylamine to diphenylamine over noble metal catalysts has already been proposed (DE-OS (German Published Specification) 3,801,754).

The aforementioned processes require starting materials that are relatively costly to prepare, such as N-cyclohexylidene-aniline or dicyclohexylamine, and require improvement for a process to be performed industrially.

A process for preparing diphenylamine is proposed in DE-OS (German Published Specification) 2,249,089, in which aniline vapour is passed over an aluminum oxide catalyst that is or has been treated with boron trifluoride. However, the space-time yields that can be achieved are low for industrial production of diphenylamine.

According to German Patent Specification 530,736 aniline and phenol are reacted at elevated temperature in the presence of catalysts (kaolin or bleaching earth) treated with acids. Although the reaction is carried out with an excess of aniline, some of the aniline is lost.

SUMMARY OF THE INVENTION

The invention relates to a process for preparing diphenylamines of the formula

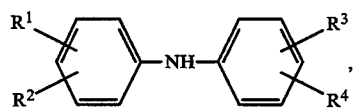

in which $R^1$, $R^2$, $R^3$ and $R^4$ denote, independently of one another, hydrogen, $C_1$–$C_4$-alkyl or $C_1$–$C_4$-alkoxy, which is characterised in that anilines of the formula

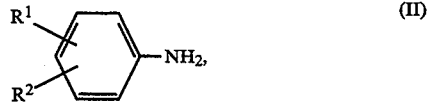

are reacted with cyclohexanones of the formula

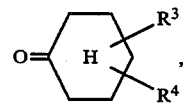

which may be present mixed with recycled reaction products, in the formulae the radicals $R^1$–$R^4$ having the above meaning and aniline and cyclohexanone being present in a molar ratio of 1:4–6:1, preferably 1:2–5:1, over a supported catalyst containing 0.05–5% by weight, preferably 0.05–4% by weight, particularly preferably 0.1–3% by weight, based on the total weight of the catalyst, of one or more metals having a dehydrogenating action, at 200°–450° C. and at 0.1–20 bar, the metal(s) belonging to the group comprising Ru, Pd, Os, Ir, Pt, Fe, Co, Ni, Re, Mn, Cu, Ag, Cr and Ce.

DETAILED DESCRIPTION OF THE INVENTION

In the process according to the invention condensation of aniline and cyclohexanone apparently occurs first of all, from which it may be assumed that the condensation proceeds, via the elimination of water, to the formation of N-cyclohexylidene-aniline, which is then dehydrogenated to diphenylamine. The successful course of the process according to the invention is surprising for various reasons. For example, it is known that the formation of N-cyclohexylidene-aniline is an equilibrium reaction, which always involves the presence of significant amounts of the starting products. Accordingly, one always had to accept the risk that cyclohexanone is substantially aromatised to phenol, which is of no value for the purposes of this process. Furthermore, it might have been expected that the intermediate formation of N-cyclohexylidene-aniline is not particularly favoured, since extremely acidic catalysts are necessary for its formation.

The process according to the invention contains a further surprise in as much as not only does the substantial formation of phenol from cyclohexanone, as described above, not take place, but even added phenol reacts as if it were cyclohexanone, and thus in the context of the aforedescribed conceptual model there must even take place a conversion of phenol into cyclohexanone. The amount of this added phenol, which should exhibit the same substitution pattern as the cyclohexanone used in order to avoid unnecessary product mixtures, is 0–20 mol %, based on the total amount of the mixture of cyclohexanone and phenol.

However, the case of a net production of phenol, for example with higher molar ratios of cyclohexanone to aniline, is also permissible according to the invention since phenol can be separated off in the course of a distillative working-up of the reaction mixture. Such a separation takes place preferably together with unreacted aniline. This provides, for example, the following possible uses for the phenol: 1. in the case of small amounts of phenol the phenol-aniline mixture can be worked up into pure aniline, the small phenol fraction being combusted for example; 2. the phenol-aniline mixture can be recycled with an altered cyclohexanone-aniline molar ratio to the process according to the invention; 3. the phenol-aniline mixture in the case of a relatively large phenol fraction can for example be passed on for hydrogenating conversion to dicyclohexylamine, or used for another suitable purpose. Phenol is therefore permitted to be present in the reaction mixture of the process according to the invention in the range 0–25% by weight, preferably 0.1–20% by weight, based on the total reaction mixture.

The catalyst to be used according to the invention contains one or more metals from the group comprising Ru, Pd, Os, Ir, Pt, Fe, Co, Ni, Re, Mn, Cu, Ag, Ce and Cr. The metals are present in a total amount of 0.05–5% by weight, preferably 0.05–4% by weight, particularly preferably 0.1–3% by weight, based on the total weight of the catalyst. Preferably, one or more metals from the group comprising Pd, Ir, Pt, Co, Ni, Re, Mn, Ce and Cr is/are present.

Furthermore, the catalyst to be used according to the invention preferably contains a combination of Pt with at least one of the aforementioned other platinum metals or Re, in which Pt is present in an amount of 10–90% of the total weight of all metals. In a particularly preferred embodiment Pt is combined with Pd, Ir or Re, or a mixture of Pd, Ir and Re. In an especially particularly preferred embodiment Pd, Ir or Re alone is used for combination with Pt. In such a combination the proportion of Pt is 10–90%, preferably 15–80%, particularly preferably 20–70%, of the total weight of all noble metals.

The catalyst to be used furthermore contains 1–12% by weight, preferably 2–10% by weight, based on the weight of the catalyst, of one or more alkali metal hydroxides and/or alkali metal sulphates, the hydroxide and sulphate proportions being in each case at most 6% by weight, preferably in each case at most 5% by weight. Examples of such hydroxides and sulphates are lithium hydroxide, sodium hydroxide, potassium hydroxide, rubidium hydroxide, caesium hydroxide, preferably lithium hydroxide, sodium hydroxide or potassium hydroxide, and particularly preferably sodium hydroxide or potassium hydroxide; lithium sulphate, sodium sulphate, potassium sulphate, rubidium sulphate, caesium sulphate, preferably lithium sulphate, sodium sulphate or potassium sulphate, and particularly preferably sodium sulphate or potassium sulphate.

The aforementioned constituents of the catalysts to be used are arranged on a support. Examples of such supports are aluminium oxide, aluminium spinel, activated charcoal, silica gel, bentonite, pumice, zirconium oxide, titanium oxide, zinc oxide, magnesium oxide and also oxides of the rare earths. The last-mentioned oxides may also be doping constituents of the first-mentioned supports.

The aforementioned constituents of the catalysts to be used are preferably applied to a support of aluminium oxide or an aluminium spinel, particularly preferably to such an aluminium oxide or aluminium spinel as has been treated with manganese and chromium or cerium. Suitable forms of aluminium oxide are in particular the α- and γ-modifications. Aluminium spinels are compounds of the formulae $Me(II)Al_2O_4$ and $Me(I)AlO_2$ in which Me(II) is a divalent metal cation of iron, zinc, nickel, copper, cobalt, cadmium, magnesium or other metals, preferably of magnesium, and Me(I) is a monovalent cation, for example lithium (lithium-aluminium spinel). The aluminium in the spinels may be partly replaced by trivalent iron, chromium or manganese. The preferred support is $Al_2O_3$, particular preference being given to γ-$Al_2O_3$. Such a support particularly preferably contains chromium and manganese together in an amount of about 0.05–8% by weight, preferably 0.2–5% by weight, based on the total weight of the catalyst. The weight ratio of chromium to manganese is 5:1–1:5, preferably 2:1–1:2. Such supports treated with chromium and manganese are known from European Patent Specification 208,933.

In order to prepare the aforedescribed catalysts, a preferred procedure comprises applying compounds of chromium and manganese to an $Al_2O_3$ in the form of extrusion mouldings, pellets or spheres having dimensions of about 2–10 mm, heating the thus treated support at an elevated temperature, and then applying separately the dehydrogenating metals and one or more of the alkali metal hydroxides and/or one of more of the alkali metal sulphates; after each application the support is dried, generally at 100°–140° C. under reduced pressure up to atmospheric pressure, for example 1–1000 mbar, preferably 10–500 mbar, for example in a water jet vacuum.

The application of the chromium and the manganese to the catalyst support may be effected for example by joint precipitation of a mixture of manganese and chromium hydroxides from a solution of chromium and manganese salts using an alkali metal hydroxide or ammonia, followed by washing out the soluble fractions with water. Suitable chromium and manganese salts are in particular the sulphates, chlorides, acetates and/or nitrates of the stated elements. The chromium and manganese can also be deposited on the catalyst support in the form of ammonium-manganese chromate or chromium-alkali metal-manganese chromate from a solution of manganese(II) salts and ammonium bichromate using ammonia and/or basic alkali metal compounds. Particularly uniform and adherent deposits are obtained if the addition of the base takes place slowly and uniformly, avoiding relatively large differences in concentration.

To this end the precipitation may for example be performed by means of urea under hydrolysing conditions, whereby the conditions of the slow addition of base are ensured particularly effectively.

After the application of the chromium and manganese compounds and the described precipitation, the thus treated catalyst support is washed free from soluble compounds before being heated at elevated temperatures (for example 200°–450° C., preferably 250°–350° C.). After this heat treatment the support carrying deposited chromium and manganese is ready to be impregnated with the remaining catalyst constituents mentioned.

Instead of chromium, cerium or another rare earth element may also be used. A detailed description of the preparation of this catalyst is given in DE-OS (German Published Specification) 4,107,395.

The impregnation of the catalyst support with the metals and with alkali metal hydroxide and/or alkali metal sulphate (in each case one or more of the latter) takes place separately. This procedure may be performed for example by first of all impregnating the support with the metals, for example in the form of aqueous solutions of their chlorides, nitrates, acetates or other suitable salts, following which the support is dried and is subjected to a further impregnation with a solution of alkali metal hydroxide and/or alkali metal sulphate. In this treatment the metals are precipitated in the form of their oxides or hydroxides. The impregnation with the alkali metal hydroxide or hydroxides and with the alkali metal sulphate or sulphates may take place separately or jointly. After a final drying the catalyst is ready for use.

In a preferred embodiment the catalyst is activated before use by treatment with hydrogen at elevated temperature, for example at 120°–400° C., preferably at 150°–380° C. This activation may take place particularly advantageously in the rector in which the preparation of diphenylamine according to the invention subsequently takes place.

However, the support can also first of all be impregnated with an alkali metal hydroxide solution and then dried, following which the aforementioned salts of the metals are applied to the thus pretreated catalyst support which has been rendered basic, the precipitation of the metals in the form of their oxides or hydroxides also occurring during the impregnation. With this variant the additional impregnation with alkali metal sulphates can take place together with the alkali metal hydroxide, before or after the impregnation with the alkali metal hydroxide or as a concluding impregnation after the application of the metals. Here too, a separate drying is performed after each impregnation procedure. After the subsequent drying the catalyst is also again ready for use, though it can also be activated beforehand with hydrogen at elevated temperature as described hereinbefore.

Instead of impregnating the said support in order to deposit the aforementioned substances, the support can also be sprayed with suitable solutions. The equipment required for all these procedures and the adjustment of the desired deposition by selecting the amount and concentration of the solutions of the aforementioned elements are in principle known to the person skilled in the art.

In addition to aqueous solutions, in principle alcoholic solutions or solutions in lower carboxylic acids or lower amines are also suitable as long as the intended salts of the metals or the basic alkali metal compounds or the sulphates are soluble therein.

$C_1$-$C_4$-Alkyl or $C_1$-$C_4$-alkoxy in the substituents $R^1$-$R^4$ are for example methyl, ethyl, propyl, isopropyl, butyl, isobutyl, methoxy, ethoxy, propoxy, isopropoxy, butoxy or isobutoxy. Preferably the aforementioned substituents have 1-2 carbon atoms, and particularly preferably they are methyl or methoxy. In addition, the substituents $R^2$ and $R^4$ are preferably hydrogen, while the substituents $R^1$ and $R^3$ may be chosen from the whole range of aforementioned substituents. The process is particularly preferably aimed at the preparation of unsubstituted diphenylamine.

The starting compounds aniline and cyclohexanone or aniline and a cyclohexanone/phenol mixture are used in a molar ratio of 1:4–6:1, preferably 1:2–5:1. The starting compounds are vaporised individually or together and the resultant vapour mixture is applied, if necessary using a carrier gas stream, to the aforedescribed catalyst.

Suitable carrier gases for this purpose are for example nitrogen, hydrogen, argon, lower hydrocarbons such as methane, ethane or natural gas, and also mixtures thereof. Preferably, nitrogen or hydrogen, or a mixture thereof, are used as carrier gases. The carrier gas is employed in an amount of 1–100 l/g of starting material, preferably 1–50 l/g of starting material. The space velocity over the catalyst is fixed at 0.01–1 kg of starting material per l of catalyst per hour.

In addition to the aforementioned starting compounds aniline and cyclohexanone and the already described partial replacement of cyclohexanone by the corresponding phenol, further substances such as N-cyclohexylidene-aniline, dicyclohexylamine or N-cyclohexyl-aniline may be used.

The process according to the invention is carried out in the gaseous phase at a temperature of 200°–450° C., preferably 200°–400° C., and at a pressure of 0.1–20 bar, preferably 1–6 bar. The combination of reaction temperature and reaction pressure are chosen in a manner known to the person skilled in the art so that the process can always be carried out in the gaseous phase.

EXAMPLE 1

200 g of a commercially available $\gamma$-$Al_2O_3$ (spherical diameter 2–5 mm) having a specific surface area of 350 m²/g were impregnated overnight with a solution that had been prepared from 2.66 g of $H_2PtCl_6$ and 533 g of water. The catalyst was then separated from the liquid and dried overnight at 100° C. The catalyst was next heat-treated for 3 hours at 350° C. in a stream of nitrogen, and was then reduced for 3 hours at 350° C. in a stream of hydrogen (50 l/h). 100 g of the catalyst were impregnated for 1 hour with a solution that had been prepared from 5 g of $Na_2SO_4$ and 115 g of water. The excess solution was then removed. After a further intermediate drying the catalyst was impregnated with a solution of 3 g of NaOH in 35 ml of water and re-dried before use.

A reaction tube 17 mm in diameter and 70 cm long was filled in its middle part with 15 ml (13.6 g) of the described catalyst; the upper part was filled with packings and served as evaporation zone. The catalyst was first of all activated for 66 hours at a temperature of 400° C. in a stream of hydrogen (20 l/h). Using a calibrated metering apparatus, a mixture of 1 mol of aniline and 2 mol of cyclohexanone was reacted at 340° C. over the catalyst. 486 g of the mixture were passed in the course of 66 hours together with hydrogen (2 l/h) and nitrogen (5 l/h) into the reaction tube. The reaction product was condensed and analysed by gas chromatography. The product had the following composition:

| | |
|---|---|
| Diphenylamine | 46.6% |
| N-Cyclohexylaniline | 3.7% |
| N-Cyclohexylideneaniline | 6.7% |
| Carbazole | 0.8% |
| Aniline | 18.5% |
| Phenol | 15.6% |
| Cyclohexanone | 7.5% |
| By-products | Remainder making up 100% |

EXAMPLE 2

$\gamma$-Aluminium oxide (extrusion mouldings, $\phi=4$ mm) with a specific surface area of 230 m²/g was impregnated in the same way as described in Example 1 with $H_2PtCl_6$, $Na_2SO_4$ and NaOH. 15 ml (9.7 g) of the thus prepared catalyst were heated at 300° C. in a stream of hydrogen (30 l/h) using the reaction tube described in Example 1, and maintained for 18 hours at this temperature. The furnace temperature of the reaction tube was then raised to 320° C. and the reaction was carried out, A mixture containing aniline and cyclohexanone in a molar ratio of 1:1 was reacted at this temperature. 683 g of the mixture were passed within 140 hours together with hydrogen (2 l/h) and nitrogen (5 l/h) into the reaction tube. The reaction product was condensed and analysed. The product had the following composition:

| | |
|---|---|
| Diphenylamine | 42.3% |
| N-Cyclohexylaniline | 47.8% |
| N-Cyclohexylideneaniline | 6.6% |
| Aniline | 1.9% |
| Phenol | 0.1% |
| By-products | Remainder making up 100% |

The temperature of the reaction furnace was then raised to 370° C. and a further 901 g of the aniline-cyclohexanone mixture were passed over the catalyst over the course of 164 hours. The condensed reaction product had the following composition:

| | |
|---|---|
| Diphenylamine | 57.1% |
| N-Cyclohexylaniline | 28.4% |
| N-Cyclohexylideneaniline | 10.7% |
| Aniline | 1.0% |
| Phenol | 0.5% |
| By-products | Remainder making up 100% |

EXAMPLE 3

400 g of a commercially available $\gamma$-$Al_2O_3$ (spherical diameter 3–8 mm) with a specific surface area of 330 $m^2/g$ were impregnated with a solution that was prepared from 10 g of $H_2PtCl_6$ and 1,060 g of $H_2O$. The procedure was the same as described in Example 1.

100 g of the reduced Pt catalyst were however this time impregnated with a solution that had been prepared from 2 g of $Re_2O_7$ and 32 g of water. After a further intermediate drying 20 ml (13 g) of the thus post-treated Pt catalyst were activated at 400° C. for 66 hours in a stream of hydrogen (60 l/h). A mixture containing aniline and cyclohexanone in a molar ratio of 1:2 was then reacted for the diphenyl preparation according to Example 1, 472 g of the reaction mixture being passed together with hydrogen (2 l/h) and nitrogen (5 l/h) into the reaction tube. The condensed reaction product had the following composition:

| | |
|---|---|
| Diphenylamine | 36.6% |
| N-Cyclohexylaniline | 3.8% |
| N-Cyclohexylideneaniline | 20.5% |
| Cyclohexanone | 9.7 |
| Aniline | 14.5% |
| Phenol | 8.9% |
| By-products | Remainder |

EXAMPLE 4

100 g (63 ml) of zirconium dioxide tablets of size ⅛ and a specific surface area of 50 $m_2/g$ were impregnated with a solution that was prepared from 2.08 g of Pd acetate and 25 g of methylene chloride. 20 ml (33.5 g) of the tablets dried at 120° C. were used for the reaction of aniline and cyclohexanone in a molar ratio of 1.7:1. 701 g of the aniline-cyclohexanone mixture were reacted at 270° C. over the course of 195 hours. The condensed reaction product had the following composition:

| | |
|---|---|
| Diphenylamine | 27.1% |
| N-Cyclohexylaniline | 10.6% |
| N-Cyclohexylideneaniline | 0.1% |
| Phenol | 36.2% |
| Aniline | 11.9% |
| By-products | Remainder |

EXAMPLE 5

100 g of a commercially available $\gamma$-$Al_2O_3$ with a specific surface area of 150 $m^2/g$, obtained in the form of an extrudate (1/16') were impregnated in the same way as the aluminium oxide in Example 1, firstly with Pt and then with $Na_2SO_4$ and NaOH.

Aniline and cyclohexanone were reacted in a molar ratio of 1:1 using 50 ml (32 g) of the catalyst prepared here. 489 g of the mixture were passed at a uniform rate over the course of 44 hours through the catalyst heated to 400° C. The condensed reaction product had the following composition:

| | |
|---|---|
| Diphenylamine | 37.9% |
| N-Cyclohexylaniline | 0.03% |
| N-Cyclohexylideneaniline | 0.1% |
| Phenol | 25.8% |
| Aniline | 30.9% |
| By-products | Remainder % |

EXAMPLE 6

100 ml of a $\gamma$-$Al_2O_3$ in spherical form (2 to 6 mm) treated with manganese and chromium according to European Patent Application 0,208,933, Example 1, were impregnated with 0.8 g of Pt in the form of an $H_2PtCl_6$ solution. 20 g (17 g) of the dried catalyst were activated in a stream of hydrogen (30 l of $H_2$/h) for 70 hours at a furnace temperature of 340° C. Aniline and cyclohexanone were reacted in a molar ratio of 1:1 at this temperature. 30 g of the mixture were passed within 26.5 hours together with nitrogen (5 l/h) through the reaction tube. The reaction product was condensed and analysed. The product had the following composition:

| | |
|---|---|
| Diphenylamine | 59.1% |
| N-Cyclohexylaniline | 1.3% |
| N-Cyclohexylideneaniline | 0.4% |
| Carbazole | 2.7% |
| Phenol | 13.2% |
| Aniline | 21.0% |
| Cyclohexanone | 0.8% |
| By-products | Remainder % |

EXAMPLE 7

400 g of a commercially available $\gamma$-$Al_2O_3$ with a specific surface of 350 $m^2/g$ and a spherical diameter of 2 to 6 mm were impregnated with a solution that had been prepared from 24.8 g of $Ce(NO_3)_3 \times 6\ H_2O$, 35.7 $Mn(CH_3COO)_2 \times 4\ H_2O$ and 100 g of water. The impregnated $Al_2O_3$ was dried and then heat-treated for 3 hours at 400° C.

200 g of the thus prepared catalyst support were impregnated with a solution that had been prepared from 8.3 g of Pd(CH$_3$COO)$_2$ and 62 g of methylene chloride. After an intermediate drying the catalyst was re-impregnated with a solution that had been prepared from 6 g of K$_2$SO$_4$ and 60 g of water. After renewed drying at 120° C., 200 ml (168 g) of the Pd catalyst were used in a vertically arranged glass tube ($\phi$32 mm) for the reaction of aniline and cyclohexanone in a molar ratio of 1:1. 808 g of the mixture were passed over the course of 24 hours over the catalyst heated to 330°–340° C. The condensed reaction product had the following composition:

| | |
|---|---|
| Diphenylamine | 64.3% |
| N-Cyclohexylaniline | 0.1% |
| N-Cyclohexylideneaniline | 0.03% |
| Carbazole | 0.9% |
| Phenol | 11.2% |
| Aniline | 20.9% |
| By-products | Remainder % |

What is claimed is:

1. A process for preparing a diphenylamine of the formula

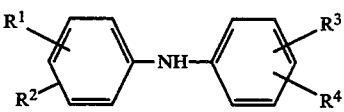

in which

R$^1$, R$^2$, R$^3$ and R$^4$ denote, independently of one another, hydrogen, C$_1$–C$_4$-alkyl or C$_1$–C$_4$-alkoxy, wherein an aniline of the formula

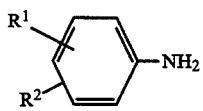

is reacted with a cyclohexanone of the formula

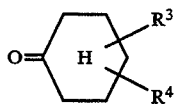

which may be present mixed with recycled reaction products, in the formulae the radicals R$^1$ to R$^4$ having the above meaning and aniline and cyclohexanone being present in a molar ratio of 1:4–6:1 over a supported catalyst containing 0.05–5% by weight, based on the total weight of the catalyst, of one or more metals having a dehydrogenating action, in the gaseous phase at 200°–450° C. and at 0.1–20 bar, and the metal(s) is/are selected from the group consisting of Ru, Pd, Os, Ir, Pt, Fe, Co, Ni, Re, Mn, Ce, Cu, Ag and Cr.

2. The process of claim 1, wherein the reaction is carried out at 200°–400° C.

3. The process of claim 1, wherein the reaction is carried out at 0.1–6 bar.

4. The process of claim 1, wherein the metal(s) is/are selected from the group consisting of Pd, Ir, Pt, Co, Ni, Re, Mn, Ce and Cr.

5. The process of claim 4, wherein Pt is used in combination with Pd, Ir, Ru, Os or Re.

6. The process of claim 1, wherein aniline and cyclohexanone are present in a molar ratio of 1:2–5:1.

7. The process of claim 1, wherein the supported catalyst contains 0.04–4% by weight, based on the total weight of the catalyst, of one or more of the metals.

8. The process of claim 7, wherein the supported catalyst contains 0.1–3% by weight, based on the total weight of the catalyst, of one or more of the metals.

9. The process of claim 1, wherein the support is aluminium oxide.

10. The process of claim 9, wherein the support is an aluminium oxide treated with manganese and chromium or cerium.

11. The process of claim 1, wherein the catalyst additionally contains 1–12% by weight, based on the total weight of the catalyst, of one or more alkali metal hydroxides and/or alkali metal sulphates, the hydroxides and sulphates in each case being present in an amount of at most 6% by weight.

12. The process of claim 1, wherein the cyclohexanone is replaced in an amount of 0–20 mol-% by the corresponding phenol.

13. The process of claim 5, wherein Pt is used in combination with Pd, Ir or Re.

14. The process of claim 13, wherein the proportion of Pt in the combination is 10–90% of the total weight of the noble metals and Re.

15. The process of claim 14, wherein the proportion of Pt in the combination is 15–80% of the total weight of the noble metals and Re.

16. The process of claim 15, wherein the proportion of Pt in the combination is 20–70% of the total weight of the noble metals and Re.

17. The process of claim 11, wherein the catalyst additionally contains 2–10% by weight, based on the total weight of the catalyst, of one or more alkali metal hydroxides and/or alkali metal sulphates, the hydroxides and sulphates in each case being present in an amount of at most 5% by weight.

18. The process of claim 10, wherein the support contains chromium and manganese together in an amount of about 0.05–8% by weight, based on the total weight of the catalyst, the weight ratio of chromium to manganese being 5:1–1:5.

19. The process of claim 10 wherein another rare earth element besides chromium or cerium is employed.

20. The process according to claim 1, wherein the substituents are H, C$_1$–C$_2$ alkyl, or C$_1$–C$_2$-alkoxy.

* * * * *